United States Patent
Waterfield Price et al.

(10) Patent No.: US 12,094,107 B2
(45) Date of Patent: Sep. 17, 2024

(54) CAD DEVICE AND METHOD FOR ANALYZING MEDICAL IMAGES

(71) Applicant: Optellum Limited, Oxford (GB)

(72) Inventors: Noah Waterfield Price, Oxford (GB); Vaclav Potesil, Oxford (GB); Timor Kadir, Oxford (GB)

(73) Assignee: Optellum Limited, Oxford (GB)

( * ) Notice: Subject to any disclaimer, the term of this patent is extended or adjusted under 35 U.S.C. 154(b) by 275 days.

(21) Appl. No.: 17/224,543

(22) Filed: Apr. 7, 2021

(65) Prior Publication Data
US 2022/0327690 A1 Oct. 13, 2022

(51) Int. Cl.
*G06T 7/00* (2017.01)
*G16H 50/20* (2018.01)
*G16H 50/30* (2018.01)

(52) U.S. Cl.
CPC .......... *G06T 7/0012* (2013.01); *G16H 50/20* (2018.01); *G16H 50/30* (2018.01); *G06T 2207/10088* (2013.01); *G06T 2207/10104* (2013.01); *G06T 2207/10108* (2013.01); *G06T 2207/10116* (2013.01); *G06T 2207/10132* (2013.01);
(Continued)

(58) Field of Classification Search
CPC ......... G06T 7/0012; G06T 2207/10088; G06T 2207/10104; G06T 2207/10108; G06T 2207/10116; G06T 2207/10132; G06T 2207/20081; G06T 2207/20084; G06T 2207/30064; G16H 50/20; G16H 50/30
See application file for complete search history.

(56) References Cited

U.S. PATENT DOCUMENTS

2009/0052763 A1 * 2/2009 Acharyya ................. G06T 7/13
382/132
2016/0130656 A1 * 5/2016 Whitney .............. C12Q 1/6886
536/24.31
(Continued)

FOREIGN PATENT DOCUMENTS

CN 111598853 A * 8/2020
WO WO-2014113786 A1 * 7/2014 ........... G01N 23/046
(Continued)

OTHER PUBLICATIONS

Machine translation of WO-2017092615-A1 (Year: 2017).*
(Continued)

*Primary Examiner* — Aaron W Carter
*Assistant Examiner* — Courtney Joan Nelson
(74) *Attorney, Agent, or Firm* — Optimus Patents US, LLC

(57) ABSTRACT

A method for analysing images in a computer aided diagnosis system (CADx) to provide a first image analysis score and a second image analysis score for an image is described. The method comprising; receiving an input comprising at least one input image showing all or part of the lungs of a subject; analysing the input to calculating a first image analysis value and a second image analysis value for the input and processing the calculated values to generate corresponding first image analysis and second image analysis scores and outputting at least one of the first image analysis score and the second image analysis score for the subject. A (Continued)

computer aided diagnosis system (CADx) and a method of training a computer aided diagnosis system are also described.

17 Claims, 4 Drawing Sheets

(52) U.S. Cl.
CPC ............... *G06T 2207/20081* (2013.01); *G06T 2207/20084* (2013.01); *G06T 2207/30064* (2013.01)

(56) References Cited

U.S. PATENT DOCUMENTS

| | | | |
|---|---|---|---|
| 2019/0131016 A1* | 5/2019 | Cohen | ................... G16H 70/60 |
| 2020/0345292 A1* | 11/2020 | Stavros | ............... A61B 8/0825 |

FOREIGN PATENT DOCUMENTS

| | | | | | |
|---|---|---|---|---|---|
| WO | WO-2016075096 A1 | * | 5/2016 | ........... | G06K 9/0014 |
| WO | WO-2016094330 A2 | * | 6/2016 | ....... | G01N 33/57423 |
| WO | WO-2017092615 A1 | * | 6/2017 | ........... | G06K 9/6221 |
| WO | 2019/057967 A1 | | 3/2019 | | |
| WO | 2019/057975 A1 | | 3/2019 | | |
| WO | 2019/073086 A1 | | 4/2019 | | |

OTHER PUBLICATIONS

Machine translation of CN-111598853-A (Year: 2020).*
R. D. Ardekani, M. Torabi and E. Fatemizadeh, "Breast Cancer Diagnosis and Classification in MR-images using Multi-stage classifier," 2006 International Conference on Biomedical and Pharmaceutical Engineering, Singapore, 2006, pp. 84-87. (Year: 2006).*
Waterfield Price Noah et al: "Prediction of adenocarcinoma among other subtypes of Lung cancer from CT using deep learning.", Journal of Clicniccal Oncology, vol. 39, No. 15_suppl, May 20, 2021 (May 20, 2021); pp. 3057-3057, XP055953957,US:CSSN: 0732-183X, DO:C: 10 .1200/ JCO. 2021. 39 ._ 15_suppl. 3057 Retrieved from the :Internet: URL:http://dx.doi.org/10.1200/JC0. 2021.39. 15_suppl.3057> *abstract *.
Avanzo Michele et al: "Radiomics and deep learning in lung cancer", Strahlentherapie Uno Onkologie, Springer Berlin Heidelberg, Berlin/Heidelberg, vol. 196, No. 10, May 4, 2020 (May 4, 2020), pp. 87J-887, XP037247911, ISSN: 0179-7158, DOI: 10.1007/S00066-020-01625-9 [retrieved on May 4, 2020] * the whole document *.
Guo Yixian et al: "Histological Subtypes Classification of Lung Cancers on CT Images Using 3D Deep Learning and Radiomics",,Academic Radiology, vol. 28, No. 9, Sep. 1, 2021 (Sep. 1, 2021), pp. e258-e266, XP55954761, Amsterdam, . NL ISSN: 1076-6332, DOI: 10.1016/j.acra.2020.06.010 * Abstract, Discussion; figures *.
EPO Application No. 22166874.2-1122; EPO Article 94(3) Communication dated Apr. 23, 2024; pp. 1-8.

* cited by examiner

CAD DEVICE AND METHOD FOR ANALYZING MEDICAL IMAGES

FIELD OF INVENTION

This invention relates to the field of Computer Aided Diagnosis (CADx) systems and methods for assisting the interpretation of medical images to support clinicians in healthcare. In particular, the field relates to Computer Aided Diagnosis systems to assist the reading and reporting of medical images by radiologists and the interpretation of the radiologist's report by the physician responsible for patient care.

BACKGROUND OF INVENTION

In the field of medical imaging, a variety of technologies can be used to investigate biological processes and anatomy. The following examples are types of scan that may be used to provide medical images: X-Ray; Computed Tomography (CT); Ultrasound (US); Magnetic Resonance Imaging (MRI); Single Photon Emission Tomography (SPECT); and Positron Emission Tomography (PET). Each type of scan is referred to as an "imaging modality".

Typically, an image scan provides a "dataset". The dataset comprises of digital information about the value of a variable at each of a plurality of spatial locations in either a two- or three-dimensional space, for example, a CT scan may provide a 3D image of the chest of a patient. Such datasets are also known as 3D medical images.

Radiologists and other clinicians can assess the medical images in the visible anatomical regions, considering both normal tissue and any lesions within the image, where the lesions may indicate diseased tissue. The assessment of the medical images can be performed with the assistance of computer aided detection (CADe) systems. CADe systems serve to detect and highlight suspicious regions in the medical images that may have been missed by a radiologist if they had not been using the CADe system. A suspicious finding may occur in a medical scan that a doctor specifically requested to check whether a disease is present, for instance a CT scan may be requested as part of a lung cancer screening program. A suspicious finding may also occur incidentally, for instance if a lung nodule is found in a CT scan taken with the purpose of examining a patient's heart. During the examination of the CT a related task referred to as Computer Aided Diagnosis (CADx) can be performed to aid in the diagnosis of detected abnormalities in the scan. CADx systems attempt to assist the clinician in classifying any findings correctly, and typically rely on the user to identify and provide the abnormalities for subsequent classification. The output of known CADx systems is typically some kind of score. That score indicates the risk or likelihood of disease, or its absence. For example, if a radiologist has identified a lung nodule in a CT scan, the CADx system can provide a score that is indicative of the risk of malignancy to assist the clinician in classifying the identified lung nodule as either a potentially malignant tumour or a benign finding. In principle, CADx systems can also provide information not only to identify disease, but to further characterise it. For example, predicting histopathological characteristics abnormalities or diseases such as the histological subtype or invasiveness of a malignant lung nodule. Despite the numerous examples of CADx in the academic literature, few CADx systems are available commercially, because there are many challenges associated with deploying practical systems. An example of a commercial CADx system is the Transpara™ product from Screenpoint™ for breast cancer characterisation from X-Ray mammograms.

Once a medical image has been assessed by a clinician, with or without the assistance of a CADe and/or CADx system, this information is then used by the clinician to decide on an appropriate next step for the patient. These decisions are made even though the outcome of a clinician's assessment of a medical image may not be a clear diagnosis, such as "benign" or "malignant". For example, in the context of lung nodules found, whether they have been found incidentally or from within a CT scan from a lung-cancer screening program, diagnoses of the malignancy of the nodule(s) are not definitive. Rather, the next steps are chosen based on the balance of probabilities, given the available information from the medical image, the patient's medical history, as well as clinical factors relating to the patient such as, age, sex and lifestyle factors. These decisions fall on a spectrum, ranging from discharging the patient (if the nodule is deemed almost certainly benign), to scheduling a follow-up CT scan after a certain amount of time (if the nodule is deemed low risk), through to investigating further using more invasive techniques (if the nodule is deemed high risk). These decisions are often informed by pre-existing guidelines for analysis of medical images.

The specific patient management decisions being informed by a medical image determine what further information needs to be obtained from the image. To illustrate this, consider the typical lung-nodule patient management process, which is as follows. Upon assessing a lung nodule in a CT scan, the image of the nodule is used to decide either to discharge the patient, schedule a follow-up CT scan (typically 3 to 12 months later), or to investigate further. Further investigation involves a PET scan and/or a biopsy. If cancer is positively diagnosed based on the biopsy result, an appropriate treatment and/or management strategy is decided upon.

In this management process there are two decision points at which different types of decisions need to be made. The first decision point is disease identification, where the primary aim is to ascertain whether a certain disease is present and to decide what further diagnostic procedures (if any) are needed, i.e. when the initial CT (and any other pre-biopsy results) is being reviewed the aim of the assessment is to work out whether cancer is considered likely present, absent, or uncertain and the decision is whether and how to investigate further. The second decision point is disease characterisation, at which point the disease is known to be present or strongly suspected to be present. Here, the primary aim is to determine the characteristics of the disease and the decision is how to manage and/or treat the disease appropriately, i.e. once the biopsy results are available and have confirmed the existence of cancer, the type of lung cancer and how advanced it is must be determined to decide how it can be best managed and/or treated.

These two decision points in lung cancer patient management are described in further detail in the following section.

Lung Cancer Disease Identification—Description

Disease identification happens when a lung nodule is first identified on a CT. This CT is known as the baseline CT. At this point in time, the aim is to assess whether the lung nodule is malignant or benign. To accomplish this, there are several next steps that may be performed, these include:

Imaging the nodule again after a certain time interval (often six months to one year), referred to as a follow-up, to identify any changes in appearance that may be indicative of its malignancy. The time interval of the follow-up is also part of this decision. For instance, a longer follow-up interval may be chosen if the assessed likelihood of malignancy is particularly low.

Repeating the CT image but at higher resolution than baseline CT, potentially with the use of a contrast agent. This is especially likely in a lung-cancer screening context as the screening CTs are low-dose CTs, which tend have a lower image quality than a standard-dose CT.

Performing a PET Scan

Performing a blood test that is sensitive to cancer cells or DNA circulating in the blood, known as a liquid biopsy.

Performing a tissue biopsy to extract some of the nodule tissue for pathological analysis.

Disease identification may occur multiple times, as it is will likely be repeated each time new information is gained. For instance, if a clinician decided to follow-up a patient after six months, they would then have two CTs taken six months apart to consider and could use this new information to again perform disease identification.

The result of disease identification in the context of cancer is a positive or negative identification of malignancy with sufficient certainty to either discharge the patient or proceed to disease characterisation. This result is referred to as a malignancy diagnosis.

Lung Cancer Disease Identification—Disease Identification Can Lead Directly t Surgery In certain cases, the patient may be referred directly for a surgical procedure to remove the nodule if there is a high suspicion of malignancy from disease identification and/or there are factors to indicate the surgery would be successful. These factors include whether the patient is likely to recover well from surgery, for instance if the nodule is in a surgically accessible location, if the risk of complications from performing a biopsy is low, if there are other conditions or diseases that would require doing a surgical procedure regardless of the presence of lung cancer, or if this is simply the patient's preference.

Lung Cancer Disease Identification—Definitive Disease Identification Requires a Tissue Biopsy Pathological analysis of biological tissue obtained either via tissue biopsy or from a surgically resected nodule, is required for positive diagnosis if a biopsy is possible. Note that, although the accuracy of tissue biopsy is not perfect and is not considered definitive if it is negative, it is the most accurate method available for cancer diagnosis and is therefore considered the gold standard.

Tissue biopsy is necessary as although assessment of CT scans, PET scans and/or liquid biopsy results can be indicative of malignancy, they are not definitive. The results of these less-invasive tests are used to inform the decision to perform a tissue biopsy or surgery. Tissue biopsy and surgery are both costly procedures that include some risk to the patient and therefore the likelihood of malignancy needs to be sufficiently high before doctors choose to perform them. There may also be other factors preventing a tissue biopsy or surgery being performed, such as patient-specific risk factors. In these cases, a less definitive diagnosis is made using less invasive disease identification methods.

Once disease identification has resulted in a positive or negative malignancy diagnosis, the patient is either discharged, in the case of a negative malignancy diagnosis, or the process progresses to disease characterisation.

Lung Cancer Disease Characterisation—Description

Disease characterisation happens once a patient has been diagnosed with lung cancer or if cancer is strongly suspected. This is typically after a tissue biopsy has been performed and the presence (or absence) of lung cancer in the extracted tissue is pathologically confirmed. The aim at this stage is to assess the characteristics of the cancer, which are referred to as the cancer characteristics; this is useful to inform prognosis and as well as to decide upon optimal treatment and management options. Cancer characteristics within this definition include but are not limited to:

Histological subtype: Lung cancer can be classified into many histological subtypes based upon its microscopic appearance. These histological subtypes can differ significantly in their pathogenesis. For instance, small-cell lung cancer tends to grow and spread faster than non-small-cell lung cancer, had a high recurrence rate, but responds well to treatment. The two most common subtypes of non-small-cell lung cancer—adenocarcinoma and squamous-cell carcinoma—differ in prognosis, in recurrence rate, and in what drugs are used to treat them.

Expression of certain proteins: Certain cancers express the PD-L1 protein to a greater extent than others and are associated with high tumour aggressiveness and a worse prognosis but are also more responsive to certain treatments.

The presence of certain mutations: There are also targeted therapies that are effective in cases where certain genetic mutations can be identified, such as epidermal growth factor receptor (EGFR) mutations or anaplastic lymphoma receptor tyrosine kinase (ALK) rearrangements.

Cancer Stage: The extent and advancement of lung cancer is classified according to its TNM stage, which represents the size and extent of the main tumour (T), the number of nearby lymph nodes the cancer has spread to (N), and whether the cancer has metastasised to other parts of the body (M). There is also an overall stage which combines all three components of the TNM stage.

These considerations are becoming increasingly important with the rise of personalised medicine, which aims to base clinical decisions about the treatment and management of cancer based on its cancer characteristics.

Disease Characterisation of Lung Cancer Requires a Tissue Biopsy

For the disease characterisation, the requirement for biological samples tends to be even greater than for disease identification. This is because many of the cancer characteristics are often only measurable by performing tests directly on cancer tissue. This does not necessarily require any further tissue extraction procedures, as the tissue from the earlier disease identification biopsy can sometimes be used for disease characterisation. However, if an insufficient amount of tissue was extracted to perform all the necessary disease characterisation tests, then another procedure, such as a second tissue biopsy, may be required.

Tissue Biopsy May Result in Complications and is Not Always Definitive

The histopathological analysis of lung cancer is made from a combination of the microscopic appearance of the tumour cells, as well as proteomic, molecular, and genomic markers.

This methodology has several disadvantages. Firstly, the invasive nature of surgery or biopsy procedures presents an inherent risk to the patient. For instance, the complication rate for CT-guided transthoracic needle biopsy is approximately 40%. Secondly, a suitable tissue sample is not always obtainable, especially for patients at risk of complications or patients with lesions that are too small and/or located such that biopsy is not a viable option. Thirdly, extraction of the nodule tissue is not always successful, and, even if malignant tissue is successfully extracted, the intratumour heterogeneity of tumours (both variation spatially over the extent of the tumour and changes over time) means that the sampled region may not be representative of the entire mass. This can potentially result in misdiagnosis and therefore poor patient management. For instance, 11% of surgeries on suspected lung cancer patients are on patients with benign disease. Finally, there is a time cost associated with pathological diagnosis, including the time taken to arrange and perform the tissue extraction procedure followed by the pathological diagnosis and communication of the results back to the managing physician.

Liquid Biopsy Has Fewer Risks But is an Imperfect Substitute for Tissue Biopsy

Recently, there has been progress in developing blood-based tests for the diagnosis of cancer, known as liquid biopsy. These tests, such as the FoundationOne® Liquid CDx and the Guardant360® CDx enable comprehensive genomic profiling of advanced stage cancer patients from a single blood draw. They can also be used to help identify the presence of EGFR mutations in non-small cell lung cancer patients. These tests are only minimally invasive compared to the biopsy-based pathological tests. However, liquid biopsy only provides a subset of the pathological information obtainable from a tissue-based biopsy. Importantly, they do not allow the histological subtype to be determined, so their use is limited to late-stage cancer patients. Furthermore, like tissue biopsies, liquid biopsies come with significant time and monetary costs.

Disease Characterisation from CT Could Help—it Has Advantages Over Liquid/Tissue Biopsy Therefore the inventors have identified that using information in CT images to inform disease characterisation could both supplement the results of other disease characterisation procedures and partly address the lack of biopsy results when they are not available and/or not possible to obtain. This could also help alleviate some of the issues with invasive, tissue-based tests. Firstly, lung CT imaging is a non-invasive, low-risk, and cost-effective procedure that is already routinely used in clinical management of patients with pulmonary nodules. These images could be reused for image-based disease characterisation and thus obviate the need for further diagnostic procedures. Secondly, a CT-based approach would be robust to tumour heterogeneity as a CT image provides a comprehensive view of the tumour as it captures the entire lesion and its surrounding environment. Thirdly, it could be applied to all nodules visible on a CT therefore would not have the same late-stage limitation that liquid biopsy has and could be applied to nodules that cannot be tissue biopsied because they are too small or inaccessible. Finally, the results could be obtained almost immediately, taking only the amount of time required to process them image, rather than days or weeks associated with pathological analysis.

Disease Characterisation from CT Could Help—There is a Radiographic Precedent

In terms of determining the histological subtype of lung cancer from a medical image, there are some radiographic features that have been shown to be associated with certain types. For instance, nodule location has an association with subtype: small-cell and squamous-cell carcinoma tends to be located more centrally whereas adenocarcinoma and large-cell carcinoma tend to occur peripherally. In addition to location, nodule cavitation is associated with squamous-cell carcinoma and different histological adenocarcinoma growth patterns have been shown to be associated with certain radiographic features, such as nodule solidity and margin pattern. Such trends are widely known, but they are difficult to incorporate into decision making and there are no current guidelines on how to use information from medical images to assess and manage nodule patients based on the suspected histological subtype of malignant (or suspected to be malignant) lung nodules. The automatic analysis of CTs enables radiographic features to be included in the analysis and hence allows such information to be used in clinical practice.

Disease Characterisation from CT could Help—Machine Learning is Better than Humans for Quantitative Image Analysis In particular, machine learning models such as neural networks represent a good alternative for predicting histology from medical images to manual, qualitative assessment of single, human-defined parameters. These models can learn, directly from data, what patterns in the nodule images to consider such that the discrimination between nodules of different histological subtypes is maximised. Automatic assessment of medical images in this way can account for these complex, but meaningful, patterns in the data that are difficult to express and quantify by humans. For instance, the appearance of any nodule spiculations, which are long tendril-like structures extending away from the nodule edge, could be informative for predicting histology but is difficult to quantify in a manner that is reproduceable across medical practitioners.

Disease Characterisation from CT Prior Art is Not Clinically Useful

State-of-the-art machine learning models have been applied to CADx in the recent academic publications. Most of these models classify the histological subtype between certain binary combinations of subtype, such as adenocarcinoma-vs-squamous-cell-carcinoma [1] and non-small-cell-lung-cancer-vs-small-cell-carcinoma [2] but there are also examples of classifying between three [3] and four different types [4]. Additionally, some models predict the existence (or absence) of specific genetic mutations, such as EGFR [5].

In these examples, the models are designed to classify between a subset of histological subtypes of malignant nodules, given a portion of a CT image of a malignant nodule as input. Consequently, they assume that all input images are of nodules that have a positive malignancy diagnosis and, furthermore, they are from the subset of the possible types the model is trained to classify between. For instance, an adenocarcinoma-vs-squamous-cell-carcinoma model is designed to take only images of adenocarcinoma or squamous-cell carcinoma tumours as input and will produce a prediction as to which of the two types the imaged nodule belongs too.

A primary usage for a CT-based histology-prediction model would be to provide a non-invasive supplement and/or replacement of tissue-based diagnosis. Since, in current clinical practice, the malignancy diagnosis and histological subtype of a lung nodule is determined from an invasive tissue biopsy, the clinical utility of a CT-based model is severely limited if it is constrained to process images of nodules for which the malignancy and possible subtypes are known. Therefore, existing state-of-the-art CT-based models add no clinical value over that provided by the biopsy.

For a CADx histology prediction system to be clinically useful it must be applicable prior to biopsy information becoming available, and therefore it must have the flexibility to process images of nodules of any possible subtype, including benign nodules, prior to a malignancy diagnosis being available. None of the prior art in the area addresses the clinical problem and instead only considers scenarios where a nodule was known to be malignant and had one of a subset of histological subtypes.

Hence, as the inventors have recognised, there is a need for a CADx system that can analyse a lung nodule for which a diagnosis is not known and provide a conjecture for what cancer subtype the lung nodule would be if it was malignant. Primarily, the output of the CADx system would be used by clinicians to decide what further investigations were needed to reduce the uncertainty associated with diagnosis. In addition, the system output could also help the doctor to decide how best to treat the patient if they considered the nodule likely to be cancer.

REFERENCES

[1] Song, Jiangdian, et al. "Non-small cell lung cancer: quantitative phenotypic analysis of CT images as a potential marker of prognosis." *Scientific reports* 6.1 (2016): 1-9.
[2] Linning, E., et al. "Radiomics for classification of lung cancer histological subtypes based on nonenhanced computed tomography." *Academic radiology* 26.9 (2019): 1245-1252.
[3] Guo, Yixian, et al. "Histological Subtypes Classification of Lung Cancers on CT Images Using 3D Deep Learning and Radiomics." *Academic Radiology* (2020).
[4] Liu, Jian, et al. "Multi-subtype classification model for non-small cell lung cancer based on radiomics: SLS model." *Medical physics* 46.7 (2019): 3091-3100.
[5] Rizzo, Stefania, et al. "CT radiogenomic characterization of EGFR, K-RAS, and ALK mutations in non-small cell lung cancer." *European radiology* 26.1 (2016): 32-42.

SUMMARY OF THE INVENTION

Accordingly, the invention seeks to mitigate, alleviate or eliminate one or more of the abovementioned disadvantages singly or in any combination.

According to the invention there is provided a method for analysing images in a computer aided diagnosis system (CADx) to provide a first image analysis score and a second image analysis score for an image comprising; receiving an input comprising at least one input image showing all or part of the lungs of a subject; analysing the input to calculate a first interim image analysis value and a second interim image analysis value for the input and processing the calculated interim values to generate corresponding first image analysis and second image analysis scores and outputting at least one of the first image analysis score and the second image analysis score for the subject.

Preferably, the input is received at a feature encoder to analyse the input data and encode the input data to provide feature descriptors used to calculate the first image analysis value and the second image analysis value.

Further preferably the input further comprises one of more of: biomarkers or clinical parameters for the subject; wherein the biomarkers and clinical parameters comprise: subject age, subject sex, family and clinical history, results of blood tests, results of tests based on lung tissue samples, results of lung function tests.

In a preferred embodiment of the invention, the analysing of the input data is done with a machine learning model, using a neural network that is one of a convolutional or a recurrent neural network.

In a further preferred embodiment of the invention, the output circuit will not output the second image analysis score according to the calculated first image analysis score, or the calculated value for the second image analysis score.

Preferably, at least one of the first image analysis score and the second image analysis score score is calculated using a mapping function on the feature descriptor.

In a preferred embodiment of the invention, the second image analysis score comprises one or more of a histological subtypes score, a PD-L1 score, or one of more mutation scores.

Preferably, the output is textual, visual or audio output. Further preferably, the input image is one of: a CT image, an MRI image, a PET image, an X-ray image, an ultrasound image or a SPECT image.

In a preferred embodiment of the invention, the input comprises two or more input images of the same subject, where the time period between images is between 1 day and 1 year.

Preferably, the first image analysis score is a disease prediction score, and the second image analysis score is at least one disease characterization score.

Further preferably, at least one of the first image analysis score or the second image analysis score is accompanied by a certainty measure associated with the score.

In a further embodiment of the invention there is provided a computer aided diagnosis image analysis and characterisation system comprising: an input circuit configured to receive at least one input image showing all or part of the lungs of a patient; an analysis and score circuit configured to: analyse the at least one input image to identify a feature description comprised of at least one feature derived from the input image; calculate a first interim image analysis score and a second interim image analysis score; process the calculated interim values to generate corresponding first image analysis and second image analysis scores; and an output circuit for outputting the first image analysis score and the second image analysis score for the subject.

Preferably, the analysis and score circuit further comprises a feature encoder to receive the input image and identify the feature descriptor.

In a preferred embodiment of the invention, the first image analysis score and the second image analysis score is calculated by applying a mapping function to the feature descriptor.

In a further preferred embodiment of the invention, the first image analysis score is a disease prediction score, and the second image analysis score is at least one disease characterization score.

According to an embodiment of the invention there is also provided a method for training a Computer Aided Diagnosis system as described above comprising the steps of: providing a machine learning model to be trained using multiple inputs; providing training data as an input of at least one input image and at least one ground truth label to the machine learning model of the CADx system; optimising the input to obtain a prediction output comprising a first image analysis score and a second image analysis score; updating the machine learning model based on the prediction output and repeating the steps until all of the multiple inputs have been provided to the machine learning model.

Preferably, the input further comprises additional input data from an imputer to provide data corresponding to missing data in the original input.

Further preferably, the input further comprises data that has been selected for a specific population subset.

In a preferred embodiment of the invention, the input further comprises data that represents a benign lung nodule with no disease characterization.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION

Overview of the CADx System for Disease Characterisation

Figure 1:
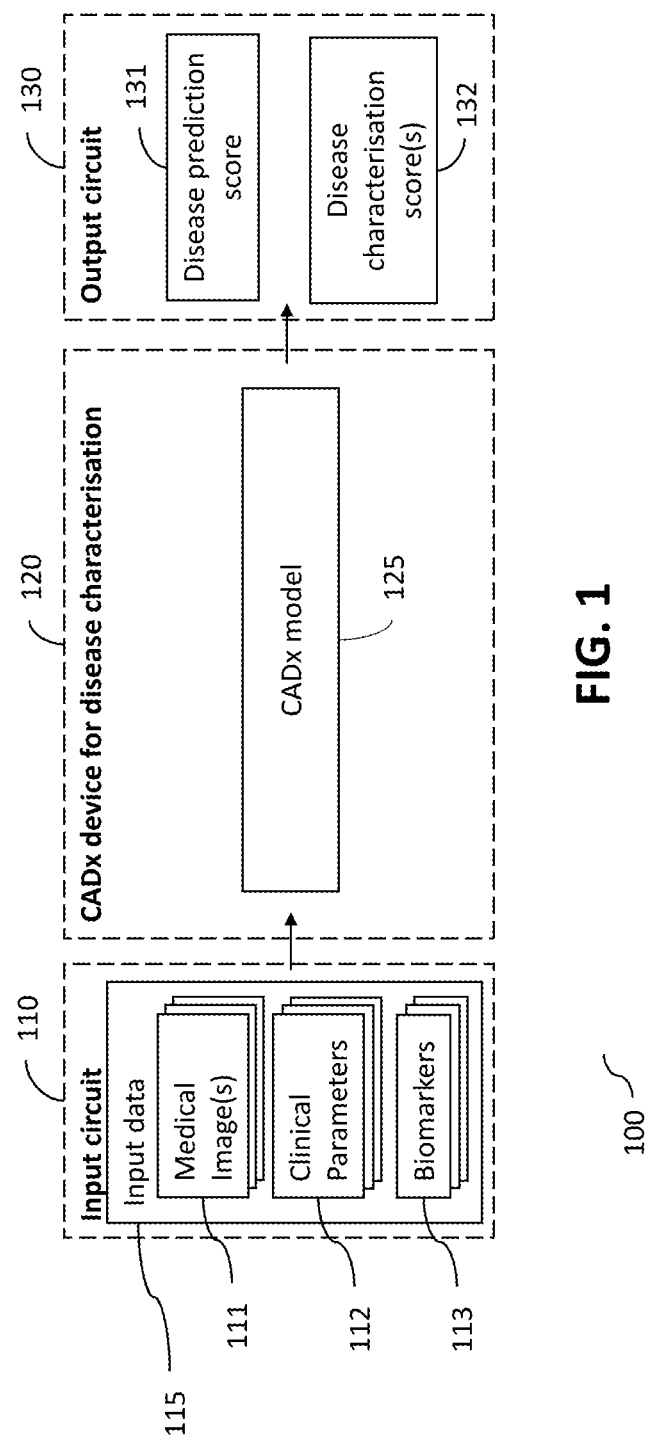
FIG. 1 illustrates a CADx system according to an embodiment of the invention.

FIG. 1 shows the CADx system (100) for analysing scan images for disease prediction and characterisation so that a patient can be referred for diagnosis if required, according to an embodiment of the invention. In the embodiment of the invention as described, the CADx system is for the analysis of CT scans showing all or a part of the patient's lungs to determine the presence of lung nodules. However, the invention is applicable to other types of imaging methodologies, and also other organs or regions of the body. The CADx system for analysing images for providing first and second image analysis scores, which in a preferred embodiment of the invention are a disease prediction score and at least one disease characterisation scores is not merely limited to processing input data corresponding to lung nodules for which the malignancy diagnosis is known. Instead, as it produces outputs corresponding both to disease characterisation and disease prediction, it can process input image data for lung nodules that do not have a diagnosis. In the preferred embodiment of the invention, the input data may be from medical image scans that may show either benign or malignant nodules.

As shown in FIG. 1, in a preferred embodiment of the invention, the input data (115) comprises one or more medical scan images (111). Preferably the image scan is a CT scan, but other imaging modalities may also be used to produce the scan, such as X-Ray; Ultrasound (US); Magnetic Resonance Imaging (MRI); Single Photon Emission Tomography (SPECT); and Positron Emission Tomography (PET). In an embodiment of the invention, the one or more medical images may be provided in combination with one or more clinical parameters (112) such as patient age and sex, weight, family and clinical history, results of blood test, results of lung function tests, and the result of one or more relevant tests such as biomarkers (113). A biomarker is defined as the result of a test that measures something within the human body or its products. An example of such a test is a liquid biopsy and an example of a biomarker is the measured amount of a certain protein such as PDL1 (programmed cell death-ligand 1) in the blood sample. In a preferred embodiment of the invention the lung disease is lung cancer.

Given some input data (115) provided via the input circuit (110), in an embodiment of the invention, the CADx device for analysing images for providing first and second image analysis scores (120) produces two outputs provided using the output circuit (130): the first output is an image analysis score, and in a preferred embodiment of the invention it is one or more disease prediction scores (131). The second output is a second image analysis score, and in a preferred embodiment of the invention this is at least one disease characterization score (132) for the input image. The first and second image analysis score outputs are obtained from a first interim image analysis value that can be used to determine disease prediction values and a second interim image analysis value used to determine disease characterisation values, as provided by the CADx model (125) within the CADx device, which performs a sequential series of mathematical operations on the values in the input data to produce the disease prediction and the disease characterisation values.

In the preferred embodiment of the invention the first and second image analysis scores are a disease prediction score (131) and at least one disease characterization score (132) for the input image and are provided via the output circuit (130). Preferably, the first and second image analysis scores, that preferably correspond to the disease prediction score and the disease characterization score that are output can be provided as text, or an image, or some other visual, graphical, textual, or audio output. For example, in an embodiment of the invention where the at least one disease characterisation scores (132) relate to histological subtype prediction, the outputs may be as follows. For the second image analysis score, corresponding to a disease characterisation score in the preferred embodiment of the invention, is a sequence of numbers each between 0 and 100, each one corresponding to the predicted likelihood of a nodule being of a particular subtype.

For instance, five image analysis scores respectively indicating the likelihoods of the histological subtype of the lung nodule shown on the input image being: adenocarcinoma, squamous-cell carcinoma, large-cell carcinoma, small-cell carcinoma, or another subtype. If the lung nodule had characteristics that were indicative of it being an adenocarcinoma, such as being located at the periphery of the lung, this would be indicated by the adenocarcinoma score produced by the device being a high value such as 90, with the other subtype scores being low values below 20 for example. For disease prediction, the output may be a percentage that represents the predicted likelihood of a nodule being malignant. These likelihoods may also be presented with an accompanying plot that visually represents them. The output could also be provided as text on its own, or an image, or some other visual textual or audio output.

In the preferred embodiment of the invention, the CADx model (125) within the CADx system for analysing input images to provide first and second image analysis scores, that are preferable for disease prediction and characterisation (120) is a machine learning model trained to parse the input data (115) corresponding to medical image scans that shown nodules (preferably nodules on all or part of a lung) of unknown malignancy diagnosis to produce a first image analysis score, corresponding to a disease prediction score (131) and a second image analysis score corresponding to one or more disease characterisation scores (132) for the input data.

The ability of the CADx system (100) to process input data associated with lung nodules of unknown malignancy diagnosis (115) is what enables it to be used in clinical context at a time where the output of the CADx system is useful for decision making i.e., prior to a tissue biopsy taking place, before which a malignancy diagnosis is not available.

A typical use that the CADx system (100) for outputting first and second image analysis scores, which in a preferred embodiment of the invention correspond to a disease prediction score and a disease characterisation score enables is described in the following example. The CADx system is configured to output at least a first image analysis score representing the likelihood of a lung nodule having the small-cell carcinoma histological subtype. In some embodiments of the invention a second image analysis score will also be output. A patient visits a healthcare provider for a cardiac exam involving a CT scan that will cover the area of the thorax. Incidentally, a suspicious lung nodule is spotted in the CT scan image, and the managing clinician decides to use the image analysis tool of this invention to help them choose the most appropriate care pathway for the nodule. At this point in time, the nodule's appearance on the collected image does not provide clear information, thus the clinician decides to schedule a follow-up visit in some time interval later. A typical lung nodule follow-up interval is 3, 6, or 12 months depending on the determined risk of the nodule being malignant. For the lung nodule in this example, its size and appearance would normally indicate a follow-up interval of 6 months. The first image analysis score that may be used as a disease prediction score of the CADx system confirms the clinician's assessment of the nodule's appearance as low to intermediate risk of malignancy. However, the CADx system also suggests from the second image analysis score, corresponding in this case to a disease characterisation score, that if the nodule is malignant, it has a high likelihood of being the small-cell carcinoma subtype. If the nodule were to have the small-cell carcinoma subtype, which is an aggressive, fast-growing form of cancer, it could develop significantly in 6 months. Therefore, the clinician chooses a shorter follow-up interval of 3 months.

Another use that the CADx system (100) for image analysis that may be used for disease prediction and characterisation enables is as follows. In some cases the lung nodule's size and appearance on the medical scan image could indicate the nodule is of high-enough risk to suggest a 3-month follow-up. In this example, the prediction by the CADx system, based on the first and second image analysis scores is that there is high likelihood of the nodule being an aggressive form of cancer. In the light of the information provided by the CADx system, the clinician may instead choose to recommend the patient for an invasive transthoracic needle biopsy.

The output of the CADx system (100) may not always result in a change in patient management, but rather confirm a management decision that a clinician is unsure of. For instance, consider a case where the lung nodule's size and appearance indicates that it is of low to intermediate risk and should have a follow-up scan in 6 months, but that its size is close to the threshold for referral for further investigations. The second image analysis score of the CADx system shows that if the nodule is malignant, its subtype would be a typical carcinoid, which is known to be a slow growing, non-aggressive cancer. This helps the doctor to confirm that a 6-month follow-up scan is appropriate.

Further Background on Machine Learning Models

The mathematical operations in the machine learning models are controlled by a set of model parameters. The choice of mathematical operations and the order in which they are performed are referred to as the model architecture. The model parameters are worked out in a process known as model training, so that they can identify patterns that occur in the input data whose presence is informative for the prediction and characterisation tasks that the CADx system performs. As used in regard to this invention, the term pattern refers to certain arrangements of the values in the input data that are informative for the task being performed, for example predicting whether a nodule is malignant or benign or has a certain histological subtype. Internally to the machine learning model, the mathematical operations are divided into groups of operations (there is no maximum group size, the minimum group size is 1) that are referred to as features. Each feature is sensitive to a particular set of patterns. When an input is presented to the model each feature responds to the set of patterns in the input data and outputs a value known as an activation. In an embodiment of the invention, the model combines the feature activations using another mathematical function, for example a weighted sum, to produce the model output. For instance, in a CADx system for predicting whether a lung nodule is malignant or benign the machine learning model output would be a disease prediction score (131). For multitask classification, such as predicting which one of several histological subtypes a lung nodule could be, e.g. adenocarcinoma, squamous-cell carcinoma, large-cell carcinoma, small-cell carcinoma, or an unlisted subtype, as well as whether a lung nodule is benign or malignant, there would be two model outputs which in a preferred embodiment of the invention correspond to 1) a disease prediction score (131) and 2) a disease characterisation score (132) consisting of the one or more numbers, each representing the likelihood of the nodule being one of the particular histological subtypes.

Training of the machine learning model requires a set of input data, where each datum is associated with one or more values collectively referred to as labels. For instance, in a dataset comprising of 10,000 CT scan images each with a histological subtype indicated by an integer, e.g. zero for adenocarcinoma, one for squamous-cell carcinoma, two for small-cell carcinoma, etc. and a smoking history indicated by a non-zero value in packyears, the histological subtype and smoking history are labels. Medical data is often inaccurate or incomplete, hence if the labels are to be used to train or evaluate a model, they need to be sufficiently accurate. When labels for the training data have been verified to be accurate, they are referred to as ground-truth labels.

It is important to select the training data in such a way as to avoid the machine learning model acquiring biases during training. For instance, if training a machine learning model to predict histological subtype, the distributions of training examples for each subtype should be balanced such that the correlations of characteristics such as CT scanner manufacturer or patient age reflect those found in the intended population. We define intended population to be a hypothetical population of data whose descriptive statistics match those chosen to optimize the performance of a model trained on the data. For instance, the training images for each subtype should have the same distribution of CT scanner manufacturers as one another. If one subtype had a disproportionate amount of scans from a certain CT manufacturer, the model would erroneously learn to associate said subtype and manufacturer. If balanced training data is not available, biases can be avoided by sampling the data during training in such a way as to correct for any imbalance.

During training of a machine learning model, the model parameters are preferably automatically adjusted by an optimization algorithm. The optimization algorithm measures how well the machine learning model performs at the task and works out what changes to the machine learning model parameters are needed to make the machine learning model perform better. The optimisation of the model is repeated until the model performs well on another set of data that is not used for training of the model. An example of a task is classifying the histological subtype of nodules from CT images, where model performance is measured using a label for the histological subtype diagnosis that is associated the images.

Example Implementation of the CADx System for Disease Characterisation

Figure 2:
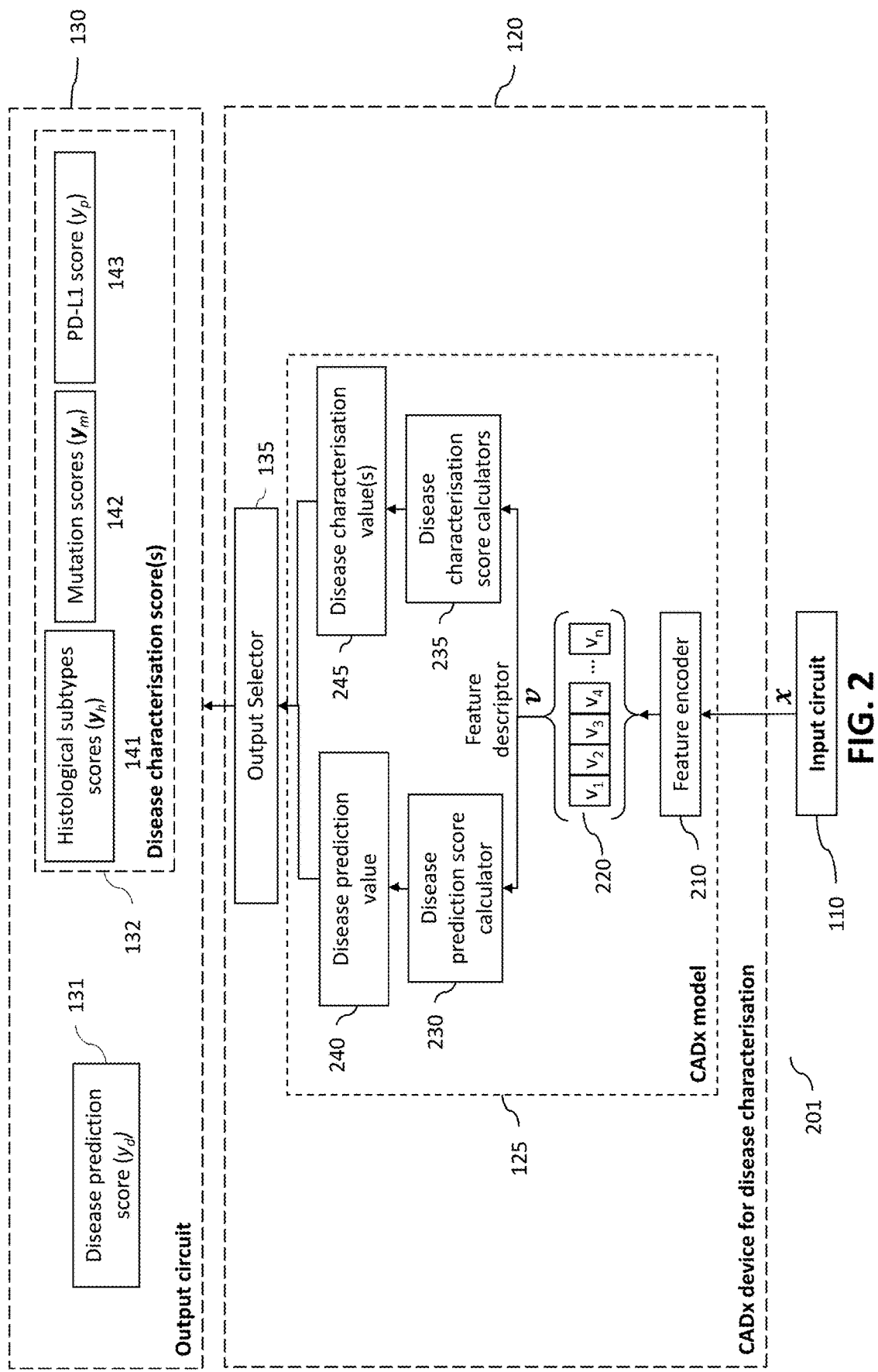
FIG. 2 show a more detailed example implementation of a CADx system of FIG. 1.

An example of a high-level implementation of the CADx system for analysing images to provide image analysis scores that may be used for disease prediction and characterisation (201) according to an embodiment of the invention is shown in FIG. 2. This shows an input circuit (110), an output circuit (130), and the CADx device for disease characterisation (120) which is comprised of a CADx model (125).

In an embodiment of the invention the CADx model (125) operates as follows: An input data unit, x (115), corresponding to one imaging study performed using a particular defined imaging modality, such as a CT scan, is first processed by the feature encoder of the machine learning model (210), which identifies the extent to which relevant patterns present in any of the input data and encodes them as a collection of feature activations referred to as the feature descriptors, v (220). Preferably the input data is received at a feature encoder to analyse the input data and encode the input data to provide feature descriptors that can be used to calculate at least one of the first interim image analysis value and the second interim image analysis value.

The score calculators (230, 235) then use the feature descriptor to calculate first and second interim image analysis values. In a preferred embodiment of the invention the first interim image analysis value corresponds to a disease prediction value (240) and the second interim image analysis value corresponds to one or more disease characterisation values (245). These interim image analysis values represent the disease prediction score (131) and disease characterization scores (132) in a raw form. For instance, each disease characterisation value may be a real number that is not restricted to a particular range. In other embodiments, each calculator may have its own feature encoder each taking the input data (115) as an input.

The first and second interim image analysis values, corresponding to disease prediction values (240) and disease characterisation values (245) are then processed by an output selector (135). The output selector can perform mathematical operations on the first and second interim image analysis values (240, 245) to transform them into the first and second image analysis scores (131, 132) for the particular subject. In a preferred embodiment of the invention the image analysis scores correspond to a disease prediction score, y (131), and disease characterization scores (132), $y_d$. For instance each disease characterisation score may be an integer ranging from one to ten. In a preferred embodiment of the invention at least one of the first and second image analysis scores is output by the output selector. Preferably, the first image analysis score is output, corresponding to a disease prediction score This transformation step may also include preventing the second image analysis score from being output, as the first image analysis score means this is not required, or that the first and second scores are not compatible, so the second score is suppressed from being output. For example, in an embodiment of the invention certain disease characterisation scores (132) are prevented from being provided to the output circuit (130), according to the calculated first image analysis score, or the calculated value for the second image analysis score, so the only output from the CADx system for analysing images will be the first image analysis score, which may correspond to a disease prediction score based on the received input.

For instance, in an embodiment of the invention, the output selector (135) may not output the histological subtype scores (141) if the disease prediction score (131) is below a certain threshold. indicating the nodule(s) in the input data (115) is most likely benign, hence making the histological subtype score likely to be invalid. In another embodiment of the invention, the output selector (135) may only output a certain disease characterisation score (or scores) (132) based on the value of another disease characterisation score (132). In another embodiment of the invention, the output selector may not perform any processing of the disease characterisation values (245) and disease prediction values (240) and simply provide them to the output circuit unaltered. In this case, the values (240, 245) and scores (131, 132) would be the same.

In a preferred embodiment of the invention, the first image analysis score is a disease prediction score that is a single score representing the likelihood that the nodule as shown on the medical scan image is a malignant nodule, $y_d$ (131)

In an embodiment of the invention, the second image analysis score, corresponding to the disease characterisation scores, y (132), for a given a unit of input data corresponding to a patient with one or more lung nodules, contains one or more of the following types of score:
- a number of scores each representing the likelihood that the lung nodule has a certain histological subtype, $y_h$ (141). For instance, this could include likelihoods for adenocarcinoma, squamous-cell carcinoma, large-cell-carcinoma, small-cell carcinoma, and a likelihood for all other subtypes.
- a number of scores each representing the likelihood that the nodule contains certain genetic mutations, for instance, this could include likelihoods for mutations such as EGFR, ALK,K-RAS, ROS-1, B-RAF, NTRK, HER-2, MET and RET mutations, $y_m$ (142).

a score representing the predicted level of PD-L1 expression. $y_p$ (143).

In an embodiment of the invention, these first and second image analysis scores, that preferably correspond to the disease prediction score and the disease characterization score are provided via the output circuit 130. In a preferred embodiment of the invention, the input to the CADx system comprises two or more input images of the same subject, where the time period between images is between 1 day and 1 year.

Example of the Physical Implementation of the Model

Figure 3:
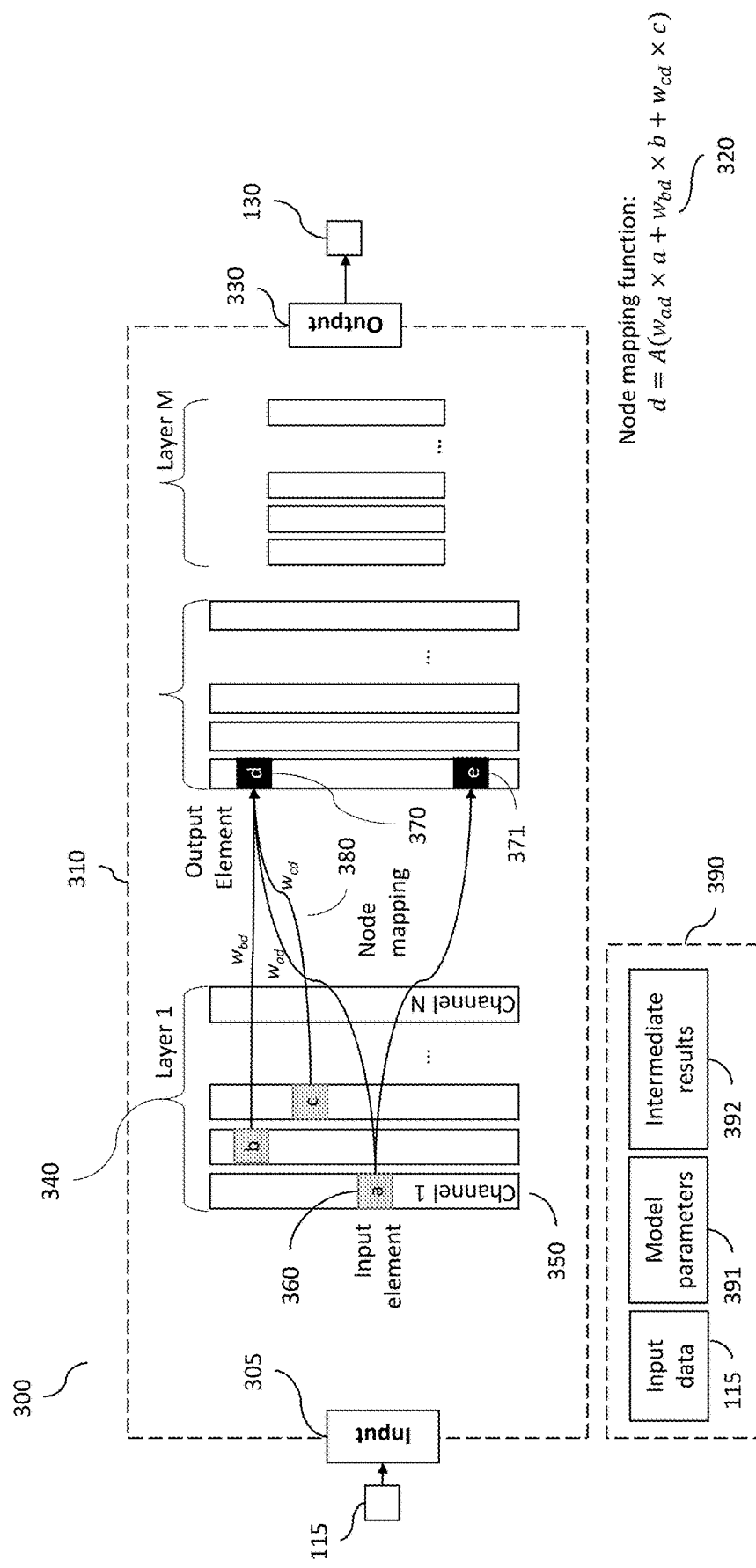
FIG. 3 shows an example of a machine learning model for a CADx system according to an embodiment of the invention.

FIG. 3 shows a neural network (310) which, in an embodiment of the invention, is an example of the type of machine learning model that the CADx model (125) may be. Preferably the neural network is a convolutional neural network or a recurrent neural network.

In an embodiment of the invention, the CADx model (125) may comprise a neural network (310), which applies a series of node mappings (380) to the input data (115) provided by the input circuit (110) to an input (305), which ultimately resolves into an output (330) consisting of one or more interim image analysis values, from which at least one of the interim image analysis values is used by the CADx device (120), to produce one or more image analysis scores, corresponding to a disease prediction score (131) and disease characterization scores (132). The input layer comprises of the value in a data input unit (115) and includes the intensities of the input medical image (111), possibly in combination with clinical parameters (112) and one or more biomarkers (113) such as patient age and sex, family and clinical history, results of blood tests, results of tests based on lung tissue samples, results of lung function tests.

In an embodiment of the invention, the example neural network (310) comprises of a consecutive sequence of at least one network layer e.g. layers in 340, each of which consists of a series of at least one channel (350). There is no maximum limit on the number of channels in each layer, and the number of channels can vary between layers. The channels (350) are further divided into at least one input element (360). Channels (350) can have varying numbers of inputs (360), and input elements (360) can be repeated in a channel (350). In this example, each input element (360) stores a single value, if more values are needed to be stored then more elements will be added to the channel (350). Some or all input elements (360) in an earlier layer are connected to the elements in a later layer by node mappings (380). Elements in layer 1 can connect to any subsequent layer. Elements (360) are connected between layers in the sense that the later element multiplies the value in the earlier element by a weight. For example, layer 1 can connect to multiple subsequent layers. At least one connection is required between layers. Unconnected, i.e. zero weight, elements serve no purpose and would normally be discarded.

The weight is modified during the training process. Once training is complete the weight is fixed. The collection of weights in the node mappings (380), together, form the model parameters (391). For each node mapping (380), the elements in the earlier layer are referred to as input elements (360) and the elements in the output layer are referred to as the output elements (370). An element may be an input element to more than one node mapping, e.g. (360), but an element is only ever the output of one node mapping function (320) e.g. (370) stores the result of a node mapping function that takes elements a, b and c as inputs, and (371) stores the result of a node mapping function that only takes element a as an input.

In order to calculate the output (330) of the neural network (310) the system first considers the input data as the earlier layer. The layers to which the earlier layer is connected by a node mapping function (320) are considered in turn as the later layer. The value for each element in later layers is calculated using the node mapping function (320) in equation 4.1, where the values in the input elements (360) are multiplied by their associated weight in the node mapping function (320) and summed together.

Node mapping function (320):

$$d = A w_{ad} \times a + w_{bd} \times b + w_{cd} \times c \qquad 4.1$$

The result of the summing operation is transformed by an activation function 'A' and stored in the output element (370). The neural network (310) now treats the previously considered later layers as the earlier layer, and the layers to which they are connected as the later layers. In this manner the neural network (310) proceeds from the input layer (340) until the values in the output (330) have been computed.

In some examples of the invention, the feature encoder (210) and the score calculators (230, 235) will each correspond to one or more layers within the neural network.

In some examples of the invention, the large number of parameters used in the neural network may require the device to include a memory (390). The memory (390) may be used to store input data (115), the model parameters (391), and intermediate results of the node mappings (392).

In some examples of the invention, another neural network can comprise the CADx model (125), which may differ from the neural network in the CADx system for disease characterisation (201) in architecture but still operate using the same principles. Hence, while the above description of a neural network refers to a particular implementation of a CADx system for disease characterisation, a skilled artisan will readily appreciate that an alternative but analogous approach can be used to construct an equivalent CADx system.

Those skilled in the art will readily appreciate that the CADx system for disease characterisation (201) can be implemented as a hardware device, a software package in a general-purpose computer, or on a firmware device such as a DSP.

Example of Training the Machine Learning Model

As described above, a computer aided diagnosis (CADx) system is used for analysing medical scan images to provide first and second image analysis scores. In a preferred embodiment of the invention, the CADx system can be trained using a machine learning model.

Figure 4:
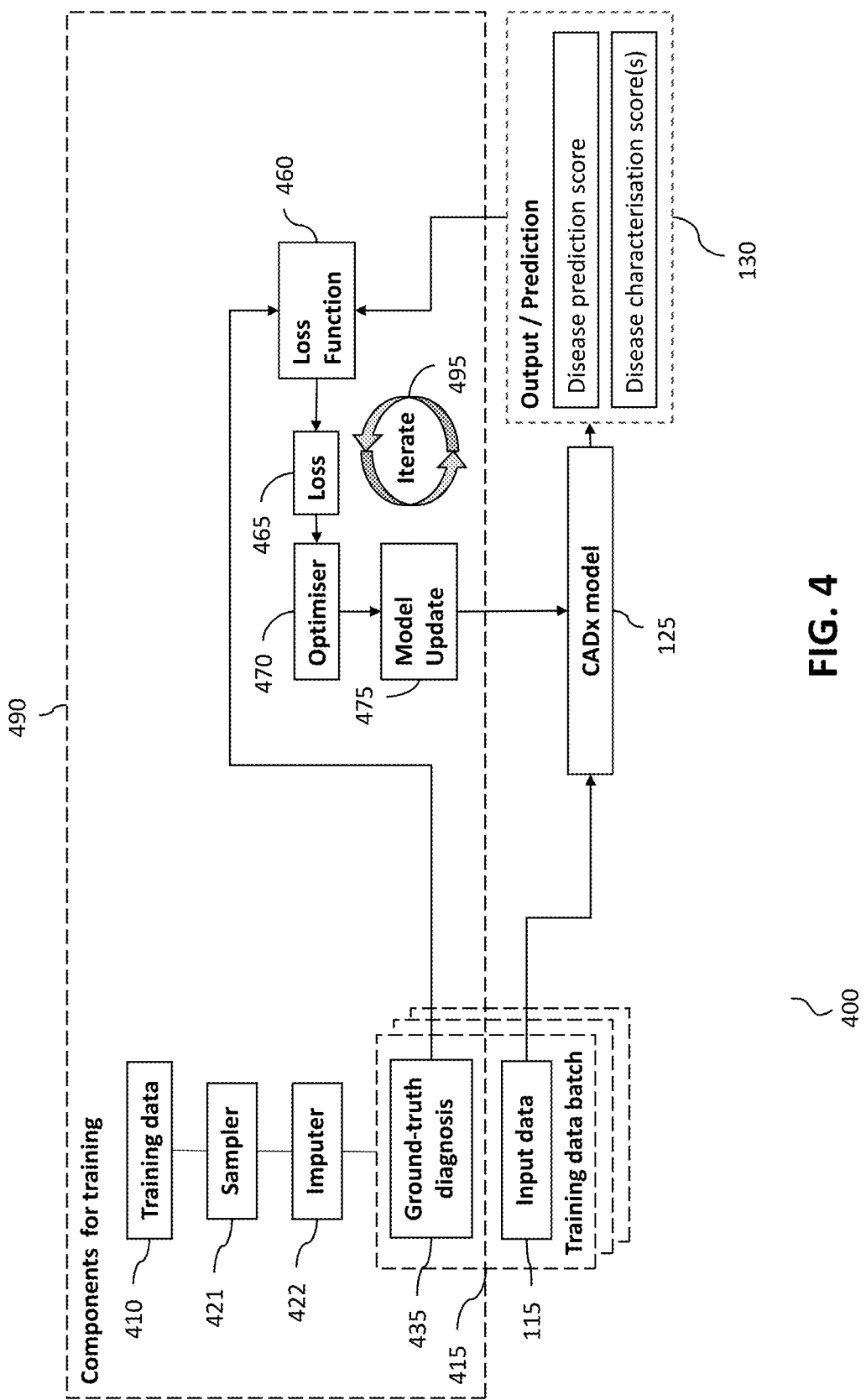
FIG. 4 shows an example of the training process for the CADx system according to an embodiment of the invention.

The process of determining the model parameters 391, w, of the neural network (preferably a convolutional or a recurrent neural network) is the network training. An example of the training procedure is shown in FIG. 4. In an embodiment of the invention of the invention, a machine learning model is to be trained using multiple inputs. In a preferred embodiment of the invention the machine learning model uses a neural network (310) which is trained using training data. Preferably the training data is provided as an input comprised of at least one input image and at least one ground truth label to the machine learning model of the CADx system. In an embodiment of the invention, a collection of input data (115), such as medical scan images from patients with their associated ground-truth disease characterisation diagnosis and malignancy diagnosis (435), is provided which constitutes the training data (410). The specific items required within the input data (115) are defined when the machine learning model is designed, and before training of the model. For example, in an embodiment of the invention, the training data may be medical images only (111), or medical images (111) plus biomarkers (113) and/or other clinical parameters. Different examples of the invention can use different items in the input data.

In some examples of the invention, the training of the neural network (310) may entail repeatedly presenting at least one subset of the training data, referred to as a training data batch (415), to the machine learning model, in a preferred example, to the neural network (310), in order to obtain the estimated first and second image analysis scores corresponding to the disease characterisation scores (132) and disease prediction score (131), for example by following the process (400) with training components 490. In an embodiment of the invention the subset of training data may have been selected to correspond to a specific population subset. In some examples of the invention, the difference between the estimated output (131, 132) and the ground-truth diagnosis (435) may be computed using a loss function (460) which computes a loss value (465) which is used to measure how accurately the machine learning model predicts the labels given the associated data. Preferably, the input data is optimised to obtain a prediction output comprising a first image analysis score and a second image analysis score. In some examples of the invention, an optimiser e.g. (470) running an optimization algorithm may be used to reduce the loss (465), i.e. improve the model's performance, by measuring how much each model parameter contributed to the loss and then using this information to apply an update (475) to the model parameters (391) in such a way as to reduce the loss (465). These steps will be repeated until all of the multiple inputs have been provided to the machine learning model. Each such modification is referred to as an iteration (495). After enough iterations, the neural network (310) can be used to produce a disease prediction score (131) and a disease characterization score (132) for new input data.

Additional Training Details

It may be the case that distribution of examples in the available training data (410) is different from the intended population. For instance, distributions of cancer subtypes can vary between countries, therefore, if the training data is sourced from a particular country but the device is intended to be used in a different country, the subtype prevalences in the training data may differ from the intended population. In this case, the intended population would likely match that of country where the device was intended to be used. To account for differences between the population of the training data (410) and the intended population, a sampler (421) may be used which selects examples for each training data batch (415) such that the distribution of data processed by the model during training matches that of the intended population. In an example of the invention, the input will be data that has been selected for a specific population subset.

It may also be the case that some examples of the invention, the training data are incomplete. This can occur in either the input data (e.g. an example that is missing clinical parameters such as patient age) and/or the ground truth diagnosis (e.g. an example that is missing cancer subtype diagnosis). Training data examples with incomplete information are a common issue when using medical data. In an embodiment of the invention if it is desired to account for incomplete examples in the training data an imputer (422) may be used to replace the missing fields with estimated values such that the data can still be used for training. The data provided by the impute will correspond to missing data in the original input. There are many methods (Molenberghs, G., Fitzmaurice, G., Kenward, M. G., Tsiatis, A., & Verbeke, G. (Eds.). (2014). *Handbook of missing data methodology*. CRC Press.) to impute missing input data (115), such as replacing a missing field e.g. patient age with the mean age across all training data or replacing it with the age of a patient from a similar, randomly-selected training-data example. If the missing data corresponds to the ground truth diagnosis (435) i.e. the labels used to train the model, the same techniques are applicable. However, there are also two further imputation methods: 1) by using the CADx device itself (120) to generate predicted labels and using these in-place of the missing ones or 2) by omitting any contributions to the loss (465) corresponding to missing labels.

In an embodiment of the invention, training a CADx model capable of both disease characterisation and disease prediction may require training the model components related to disease characterisation using training data that contains examples corresponding to patients with benign nodules, with no disease characterization. The model components associated with disease prediction require examples of data from patients both with and without cancer, whereas the model components associated with disease characterisation produce an output that may only be valid for input data corresponding to patients with cancer. Therefore, it is necessary to avoid parameter updates (475) to the model parameters (391) associated with disease characterisation that are derived from any loss (465) corresponding to training data examples from patients without cancer. One way this can be achieved is as follows: when updating model parameters associated with disease characterisation during training, contributions to the loss (465) corresponding to training data examples from patients without cancers are omitted. An alternative way this can be achieved is for the CADx model (125) to be configured such that each of the disease characterisation outputs (132) are also able to indicate that any nodule(s) represented by the input data (114) is predicted benign. For instance, consider a CADx model (125) configured to output two histological subtype scores (141), one for predicted non-small-cell carcinoma and one for predicted small-cell-carcinoma. For the output to be valid for benign nodules, an additional "subtype" score could be added for predicted benign, or equivalently, "no subtype".

Additional Functionality

In an embodiment of the invention, at least one of the first and second image analysis scores (131, 132) output by the CADx device may be accompanied by a measure of certainty associated with the score. In a preferred embodiment of the invention both of the image analysis scores will have an associated certainty measure. For neural networks, there are various methods to calculate a measure of certainty a prediction. For instance, the uncertainty of a certain score produced by the neural network (310) may be calculated by repeatedly processing the same input data (115), but each time performing a small random alteration to the neural network. For instance, this random alteration could be to set a random sample e.g. 10% of the neural network model parameters (391) to zero. Once this repeated processing has been performed and each of the scores produced have been recorded. The statistical variance of these scores can be used to calculate the uncertainty associated with the score: a broad distribution of scores indicates a higher level of uncertainty than a narrow distribution of scores. Alternatively, an analogous process could be used in which, instead of neural network being randomly altered, the input data is randomly altered. For instance, the input CT image could be cropped at a random location or it could randomly rotated or mirrored about its axes.

Advantages of Invention

In practice, image-based disease characterisation would be useful in several clinical contexts.

Firstly, as no extra procedures would be required for image-based disease characterisation (unlike tissue or liquid biopsy), it could be done simultaneously with disease identification. This would allow for decisions based on disease characterisation results to be taken earlier. For example, patients with suspected small-cell lung cancer, which has high growth rate, could be followed with a shorter imaging interval or patients with a suspected histological characteristic for which a target therapy exists (such as the EGFR genetic mutation), could be expedited to biopsy and subsequently treatment, if the biopsy result concurred.

Secondly, it could supplement disease characterisation results from other sources such as liquid biopsy and tissue biopsy. Given that these tests are not always definitive, combining the results with those obtained from an image, for instance by treating the image-based characterisation as a pre-test, may increase the overall accuracy of the biopsies.

Thirdly, when a clinician is choosing between multiple disease characterisations procedures, the disease characterisation results from the CADx system could help inform which procedures and/or tests to perform.

Finally, where a tissue biopsy is not possible, either because the nodule is too small or inaccessible and/or the patient is at high-risk of complications, an image-based method of disease characterisation may be useful, instead of or combined with a liquid biopsy. Alternatively, by providing supplementary information to a tissue biopsy, in cases where a second tissue biopsy would normally be required, the CADx system may allow this to be avoided.

This invention can be applied to predict what cancer subtype a nodule may be if it was cancer despite its actual diagnosis not yet being known. Specific scenarios include:

Aiding doctors in deciding to investigate further when a nodule is neither clearly benign nor malignant but if it were malignant would be a form of cancer that is aggressive and could increase in stage before a follow-up CT scan.

Aiding doctors in deciding whether to perform certain tests on a patient, given the predicted characteristics of a disease. For instance, if a certain genetic mutation were predicted to be likely present, a test for that mutation could be performed because of the disease characterisation score.

Improving the accuracy of medical tissue- or blood-based tests by combining the output of the CADx device with the results of a test.

Aiding doctors in avoiding the need to perform a biopsy prior to surgery when the CT provides sufficient information to work out the subtype of a suspicious lung nodule.

Aiding doctors in avoiding the need for a second biopsy to select what treatment a patient should receive when a previous biopsy has not provided sufficient information on the cancer subtype.

Aiding doctors to select an appropriate treatment for a patient when it is not possible to perform a biopsy or surgery. This may happen because the patient is at risk of complications from these procedures and/or if the nodule is in a location that is difficult to access.

Although examples of the invention have been described with reference to the CADx system being used to assist in the interpretation of chest images and lung nodules, it is envisaged that the concepts described herein may be employed beyond this area of the human body. In other examples, it is envisaged that the concepts may be applied in any medical application where it is important to consider other aspects of the clinical context, such as economic and patient preferences, where one or more medical images are being analysed.

Although examples of the invention have been described with reference to measuring lung disease identification and characterisation by reviewing images for a specific patient, it is envisaged that the concepts described herein may be employed in an automated system that examines all medical images stored on, say, a hospital database, in order to identify risk scores for other patients who, in the absence of other information, can be assumed to be of greater risk of lung disease.

Although examples of the invention have been described with reference to a CADx device, it is envisaged that the improved lung disease identification and characterisation may be employed by a nodule clinic NC manager or pulmonologist in assessing a nodule's malignancy. For example, the nodule may be of intermediate size and may appear to the NC manager to be potentially suspicious. It may also be that a lung disease risk score, is of intermediate risk, i.e. it concurs that the nodule is not obviously benign. As a consequence, the patient may be required to attend a follow-up check after a shorter interval, where the nodule is found to have grown. Subsequent biopsy could identify the nodule as being a progressive squamous cell carcinoma. Thanks to the shortened follow-up time, the cancer is identified early enough that a lobectomy procedure cures the patient, because further growth and secondary cancers never have a chance to occur.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. Therefore, some examples describe a non-transitory computer program product having executable program code stored therein for receiving at least one input medical image of a patient in which the patient's lungs are visible.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media e.g., CD ROM, CD R, etc. and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing running program or portion of a program, current program values and state information, and the resources used by the operating system to manage the execution of the process. An operating system OS is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output I/O devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

We claim:

1. A computer implemented method for analysing images in a computer aided diagnosis system (CADx) to provide at least one of a first image analysis score and a second image analysis score for an image comprising;
   receiving an input at the CADx system comprising at least one input image showing all or part of the lungs of a subject;
   analysing the input to calculate a first interim image analysis value and a second interim image analysis value for the input;
   processing the calculated interim values in the CADx system to generate corresponding first image analysis and second image analysis scores and outputting at least one of the first image analysis score and the second image analysis score for the subject; wherein the first image analysis score is a disease prediction score corresponding to a likelihood of the disease and the second image analysis score is at least one disease characterisation score corresponding to a likelihood of each of at least one disease characterisation, and
   wherein all scores are processed by an output selector circuit which performs operations on the scores to produce the output of the CADx system, resulting in the disease prediction score and the disease characterisation score being output except when either: the disease prediction score means the disease characterisation score is not required, so only the disease prediction score is output or the disease prediction score and the disease characterisation score are not compatible, so only the disease prediction score is output.

2. A method according to claim 1, wherein the input is received at a feature encoder to analyse the input data and encode the input data to provide feature descriptors used to calculate the first image analysis value and the second image analysis value.

3. A method as claimed in claim 1, wherein the input further comprises one of more of: biomarkers or clinical parameters for the subject; wherein the biomarkers and clinical parameters comprise one or more of: subject age, subject sex, family and clinical history, results of tests based on lung tissue samples, results of blood tests, results of lung function tests.

4. A method according to claim 1, wherein the analysing of the input data is done with a machine learning model, using a neural network that is one of a convolutional neural network or a recurrent neural network.

5. A method according to claim 1, wherein at least one of the first image analysis score and the second image analysis score is calculated using a mapping function on the feature descriptor.

6. A method according to claim 1, wherein the second image analysis score comprises one or more of a histological subtypes score, a PD-L1 score, or one or more mutation scores.

7. A method as claimed in claim 1, wherein the output is textual, visual or audio output.

8. A method according to claim 1, wherein the input image is one of: a CT image, an MRI image, a PET image, an X-ray image, an ultrasound image or a SPECT image.

9. A method as claimed in claim 1, wherein the input comprises two or more input images of the same subject, where a time period between images is between 1 day and 1 year.

10. A method according to claim 1, wherein at least one of the first image analysis score or the second image analysis score is accompanied by a certainty measure associated with the score.

11. A method for training a Computer Aided Diagnosis system for use in claim 1, comprising the steps of:
providing a machine learning model to be trained using multiple inputs;
providing training data as an input of at least one input image and at least one ground truth label to the machine learning model of the CADx system;
optimising the input to obtain a prediction output comprising a first image analysis score and a second image analysis score where the first image analysis score is a disease prediction score corresponding to a likelihood of the disease and the second image analysis score is at least one disease characterisation score corresponding to a likelihood of at least one disease characterisation;
updating the machine learning model based on the prediction output and
repeating the steps until all of the multiple inputs have been provided to the machine learning model.

12. A method as claimed in claim 11, wherein the input further comprises additional input data from an imputer to provide data corresponding to missing data in an original input.

13. A computer aided diagnosis image analysis and characterisation (CADx) system comprising:
an input circuit configured to receive at least one input image showing all or part of the lungs of a patient;
an analysis and score circuit configured to:
analyse the at least one input image to identify a feature description comprised of at least one feature derived from the input image;
calculate a first interim image analysis score and a second interim image analysis score;
process the calculated interim values to generate corresponding first image analysis and second image analysis scores; and
an output circuit for outputting the first image analysis score and the second image analysis score for the subject, wherein the first image analysis score is a disease prediction score corresponding to a likelihood of the disease and the second image analysis score is at least one disease characterisation score corresponding to a likelihood of each of at least one disease characterisation; and
wherein all the scores are processed by an output selector circuit which performs operations on them to produce the output of the CADx system, resulting in the disease characterisation score being output except when either: the disease prediction score means the disease characterisation score is not required, so only the disease prediction score is output or the disease prediction score and the disease characterisation score are not compatible so only the disease prediction score is output.

14. A computer aided diagnosis system according to claim 13, wherein the analysis and score circuit further comprises a feature encoder to receive the input image and identify the feature descriptor.

15. A computer aided diagnosis system according to claim 13, wherein the first image analysis score and the second image analysis score is calculated by applying a mapping function to the feature descriptor.

16. A method as claimed in claim 13, wherein the input further comprises data that has been selected for a specific population subset.

17. A method as claimed in claim 13, wherein the input further comprises data that represents a benign lung nodule with no disease characterisation.

* * * * *